(12) United States Patent
Tuominen et al.

(10) Patent No.: US 8,361,273 B2
(45) Date of Patent: *Jan. 29, 2013

(54) POLYURETHANE ELASTOMERS

(75) Inventors: Jukka Tuominen, Kuusisto (FI); Amaia Zurutuza, Pasaia (ES); Mark Livingstone, Irvine (GB); Janet A. Halliday, West Lothian (GB)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/605,689

(22) Filed: Sep. 6, 2012

(65) Prior Publication Data

US 2012/0329883 A1   Dec. 27, 2012

Related U.S. Application Data

(63) Continuation of application No. 12/373,002, filed as application No. PCT/GB2007/002415 on Jun. 27, 2007.

(30) Foreign Application Priority Data

Jul. 8, 2006  (GB) .................................... 0613638.6

(51) Int. Cl.
C09J 4/00 (2006.01)
A61K 47/00 (2006.01)
A61K 9/00 (2006.01)

(52) U.S. Cl. .................. 156/331.7; 514/772.1; 424/400

(58) Field of Classification Search ........................ None
See application file for complete search history.

(56) References Cited

U.S. PATENT DOCUMENTS

| | | | |
|---|---|---|---|
| 3,487,068 A | 12/1969 | Morozowich et al. |
| 3,565,991 A | 2/1971 | Short |
| 3,598,122 A | 8/1971 | Zaffaroni |
| 3,598,123 A | 8/1971 | Zaffaroni |
| 3,639,157 A | 2/1972 | Wunder et al. |
| 3,731,683 A | 5/1973 | Zaffaroni |
| 3,734,097 A | 5/1973 | Zaffaroni |
| 3,737,521 A | 6/1973 | Born |
| 3,760,805 A | 9/1973 | Higuchi |
| 3,797,494 A | 3/1974 | Zaffaroni |
| 3,830,907 A | 8/1974 | Short |
| 3,845,761 A | 11/1974 | Zaffaroni |
| 3,845,770 A | 11/1974 | Theeuwes et al. |
| 3,854,480 A | 12/1974 | Zaffaroni |
| 3,860,701 A | 1/1975 | Short |
| 3,867,933 A | 2/1975 | Kitrilakis |
| 3,881,043 A | 4/1975 | Rieser et al. |
| 3,892,842 A | 7/1975 | Zaffaroni |
| 3,896,819 A | 7/1975 | Zaffaroni |
| 3,901,852 A | 8/1975 | Shah |
| 3,916,898 A | 11/1975 | Robinson |
| 3,916,899 A | 11/1975 | Theeuwes et al. |
| 3,921,636 A | 11/1975 | Zaffaroni |
| 3,931,113 A | 1/1976 | Seeger et al. |
| 3,934,580 A | 1/1976 | Cournut |
| 3,941,880 A | 3/1976 | Short |
| 3,948,254 A | 4/1976 | Zaffaroni |
| 3,948,262 A | 4/1976 | Zaffaroni |
| 3,967,618 A | 7/1976 | Zaffaroni |
| 3,993,072 A | 11/1976 | Zaffaroni |
| 3,993,073 A | 11/1976 | Zaffaroni |
| 3,995,631 A | 12/1976 | Higuchi et al. |
| 4,018,918 A | 4/1977 | Ayer et al. |
| 4,034,756 A | 7/1977 | Higuchi et al. |
| 4,036,227 A | 7/1977 | Zaffaroni et al. |
| 4,041,208 A | 8/1977 | Seeger et al. |
| 4,093,708 A | 6/1978 | Zaffaroni et al. |
| 4,096,238 A | 6/1978 | Zaffaroni et al. |
| 4,098,747 A | 7/1978 | Bailey et al. |
| 4,135,514 A | 1/1979 | Zaffaroni et al. |
| 4,142,526 A | 3/1979 | Zaffaroni et al. |
| 4,202,880 A | 5/1980 | Fildes et al. |
| 4,205,115 A | 5/1980 | Piccirilli et al. |
| 4,215,691 A | 8/1980 | Wong |
| 4,235,988 A | 11/1980 | Fildes et al. |
| 4,237,885 A | 12/1980 | Wong |
| 4,250,611 A | 2/1981 | Wong |
| 4,264,757 A | 4/1981 | Park |
| 4,276,405 A | 6/1981 | Koleske et al. |
| 4,286,587 A | 9/1981 | Wong |
| 4,289,757 A | 9/1981 | Glenn |
| 4,327,727 A | 5/1982 | Prahl et al. |
| 4,379,915 A | 4/1983 | Watanabe et al. |
| 4,402,695 A | 9/1983 | Wong |
| 4,404,296 A | 9/1983 | Schapel |
| 4,426,485 A | 1/1984 | Hoy et al. |
| 4,438,225 A | 3/1984 | Peerman |
| 4,447,591 A | 5/1984 | Watanabe et al. |
| 4,466,936 A | 8/1984 | Schapel |
| 4,503,216 A | 3/1985 | Fagerburg et al. |
| 4,568,741 A | 2/1986 | Livingston |
| 4,594,240 A | 6/1986 | Kawata et al. |
| 4,596,576 A | 6/1986 | de Nijs |
| 4,647,596 A | 3/1987 | Ishii et al. |
| 4,694,238 A | 9/1987 | Norton |
| 4,707,495 A | 11/1987 | Rosenthale et al. |
| 4,731,289 A | 3/1988 | Coleman |

(Continued)

FOREIGN PATENT DOCUMENTS

DE     19842636     3/1999
DE     19742217     4/1999

(Continued)

OTHER PUBLICATIONS

Merck Index (Ninth Edition, 1976, p. 4073).

(Continued)

*Primary Examiner* — David J Blanchard
*Assistant Examiner* — Tigabu Kassa
(74) *Attorney, Agent, or Firm* — Fish & Richardson P.C.

(57) ABSTRACT

This disclosure relates to a linear polymer obtained by reacting a polyethylene glycol, a polypropylene glycol; a diol; and a diisocyanate, as well as a controlled release composition containing the linear polymer together with an active agent. The active agent can have a molecular weight of 200 g/mol to 20,000 g/mol.

17 Claims, 3 Drawing Sheets

U.S. PATENT DOCUMENTS

| | | |
|---|---|---|
| 4,767,787 A | 8/1988 | Kawata et al. |
| 4,804,691 A | 2/1989 | English et al. |
| 4,814,182 A | 3/1989 | Graham et al. |
| 4,818,517 A | 4/1989 | Kwee et al. |
| 4,894,238 A | 1/1990 | Embry et al. |
| 4,895,934 A | 1/1990 | Matier et al. |
| 4,917,686 A | 4/1990 | Bayston et al. |
| 4,931,288 A | 6/1990 | Embrey et al. |
| 4,933,418 A | 6/1990 | Sterrett |
| 4,940,588 A | 7/1990 | Sparks et al. |
| 4,945,149 A | 7/1990 | Matsumoto et al. |
| 4,952,402 A | 8/1990 | Sparks et al. |
| 4,954,043 A | 9/1990 | Yoshida et al. |
| 4,973,304 A | 11/1990 | Graham et al. |
| 5,000,955 A | 3/1991 | Gould |
| 5,002,540 A | 3/1991 | Brodman et al. |
| 5,017,382 A | 5/1991 | Embrey et al. |
| 5,023,252 A | 6/1991 | Hseih |
| 5,035,891 A | 7/1991 | Runkel et al. |
| 5,045,622 A | 9/1991 | Kohno et al. |
| 5,049,638 A | 9/1991 | Matsumoto et al. |
| 5,055,516 A | 10/1991 | Fisch et al. |
| 5,057,573 A | 10/1991 | Pascault et al. |
| 5,061,254 A | 10/1991 | Karakelle et al. |
| 5,079,009 A | 1/1992 | Embrey et al. |
| 5,100,926 A | 3/1992 | Kondo et al. |
| 5,110,598 A | 5/1992 | Kwan |
| 5,114,718 A | 5/1992 | Damani |
| 5,116,932 A | 5/1992 | Fujiwa |
| 5,118,779 A | 6/1992 | Szycher |
| 5,130,126 A | 7/1992 | Koyama et al. |
| 5,134,151 A | 7/1992 | Bartroli et al. |
| 5,156,900 A | 10/1992 | Nishimura |
| 5,159,047 A | 10/1992 | Simms |
| 5,176,907 A | 1/1993 | Leong |
| 5,178,874 A | 1/1993 | Kwan et al. |
| 5,219,663 A | 6/1993 | Kohno et al. |
| 5,219,885 A | 6/1993 | Frolich et al. |
| 5,252,602 A | 10/1993 | Alam et al. |
| 5,269,321 A | 12/1993 | MacDonald et al. |
| 5,283,297 A | 2/1994 | Miyachi et al. |
| 5,310,759 A | 5/1994 | Bockman |
| 5,312,865 A | 5/1994 | Hoefer et al. |
| 5,322,063 A | 6/1994 | Allen et al. |
| 5,324,746 A | 6/1994 | McKee et al. |
| 5,326,632 A | 7/1994 | Zenda et al. |
| 5,328,954 A | 7/1994 | Sarangapani |
| 5,354,556 A | 10/1994 | Sparks et al. |
| 5,374,704 A | 12/1994 | Muller et al. |
| 5,464,868 A | 11/1995 | Frolich et al. |
| 5,470,829 A | 11/1995 | Prisell et al. |
| 5,472,785 A | 12/1995 | Stobbie, IV et al. |
| 5,474,767 A | 12/1995 | Tremont |
| 5,505,962 A | 4/1996 | Sparks |
| 5,510,384 A | 4/1996 | McKee et al. |
| 5,514,698 A | 5/1996 | Ahmad et al. |
| 5,527,534 A | 6/1996 | Myhling |
| 5,574,102 A | 11/1996 | Tanigami et al. |
| 5,578,640 A | 11/1996 | Hanson |
| 5,578,643 A | 11/1996 | Hanson |
| 5,605,931 A | 2/1997 | Hanson |
| 5,627,254 A | 5/1997 | Oriani |
| 5,634,895 A | 6/1997 | Igo et al. |
| 5,650,171 A | 7/1997 | Quigley, Jr. et al. |
| 5,652,274 A | 7/1997 | Martin |
| 5,659,003 A | 8/1997 | Menovcik et al. |
| 5,676,939 A | 10/1997 | Tremont |
| 5,681,278 A | 10/1997 | Igo et al. |
| 5,681,850 A | 10/1997 | Frolich et al. |
| 5,686,425 A | 11/1997 | Lee |
| 5,693,319 A | 12/1997 | Tremont |
| 5,700,483 A | 12/1997 | Quigley, Jr. et al. |
| 5,710,215 A | 1/1998 | Abend |
| 5,716,676 A | 2/1998 | Schutze et al. |
| 5,723,552 A | 3/1998 | Menovcik et al. |
| 5,726,244 A | 3/1998 | McGee et al. |
| 5,726,274 A | 3/1998 | Menovcik et al. |
| 5,731,303 A | 3/1998 | Hsieh |
| 5,733,538 A | 3/1998 | Riffle |
| 5,739,113 A | 4/1998 | Lee |
| 5,744,550 A | 4/1998 | Menovcik et al. |
| 5,747,058 A | 5/1998 | Tipton et al. |
| 5,747,582 A | 5/1998 | Schutze et al. |
| 5,760,127 A | 6/1998 | Bammel et al. |
| 5,763,399 A | 6/1998 | Lee |
| 5,770,650 A | 6/1998 | McGee et al. |
| 5,777,048 A | 7/1998 | Ohrbom et al. |
| 5,780,049 A | 7/1998 | Deckner et al. |
| 5,792,810 A | 8/1998 | Menovcik et al. |
| 5,795,567 A | 8/1998 | Tremont |
| 5,817,343 A | 10/1998 | Burke |
| 5,827,925 A | 10/1998 | Tremont et al. |
| 5,827,930 A | 10/1998 | Ohrbom et al. |
| 5,827,931 A | 10/1998 | Menovcik et al. |
| 5,843,961 A | 12/1998 | Kock et al. |
| 5,849,803 A | 12/1998 | Kock et al. |
| 5,853,767 A | 12/1998 | Melman |
| 5,854,385 A | 12/1998 | McGee et al. |
| 5,855,906 A | 1/1999 | McClay |
| 5,872,195 A | 2/1999 | Green et al. |
| 5,877,216 A | 3/1999 | Place et al. |
| 5,886,039 A | 3/1999 | Kock et al. |
| 5,888,930 A | 3/1999 | Smith et al. |
| 5,891,915 A | 4/1999 | Wysor et al. |
| 5,897,879 A | 4/1999 | Friedman et al. |
| 5,900,433 A | 5/1999 | Igo et al. |
| 5,935,939 A | 8/1999 | Kararli et al. |
| 5,942,512 A | 8/1999 | Kock et al. |
| 5,942,545 A | 8/1999 | Samour et al. |
| 5,948,416 A | 9/1999 | Wagner et al. |
| 5,959,775 A | 9/1999 | Joseph et al. |
| 5,965,662 A | 10/1999 | Krebs et al. |
| 5,968,542 A | 10/1999 | Tipton |
| 5,972,372 A | 10/1999 | Saleh et al. |
| 5,973,002 A | 10/1999 | Frolich et al. |
| 5,977,172 A | 11/1999 | Yoshikawa et al. |
| 5,985,859 A | 11/1999 | Luo |
| 5,994,479 A | 11/1999 | Green et al. |
| 5,994,492 A | 11/1999 | Graham et al. |
| 6,008,312 A | 12/1999 | Shirasaka |
| 6,013,637 A | 1/2000 | Klein et al. |
| 6,022,554 A | 2/2000 | Lee et al. |
| 6,028,057 A | 2/2000 | Burns |
| 6,031,002 A | 2/2000 | Wysor et al. |
| 6,039,968 A | 3/2000 | Nabahi |
| 6,040,062 A | 3/2000 | McGee et al. |
| 6,043,224 A | 3/2000 | Lee et al. |
| 6,046,244 A | 4/2000 | Buyuktimkin et al. |
| 6,080,825 A | 6/2000 | Ohrbom et al. |
| 6,084,038 A | 7/2000 | Ohrbom et al. |
| 6,086,909 A | 7/2000 | Harrison et al. |
| 6,093,270 A | 7/2000 | Ferencz et al. |
| 6,103,256 A | 8/2000 | Nabahi |
| 6,103,765 A | 8/2000 | Neal |
| 6,103,852 A | 8/2000 | Shirasaka |
| 6,114,444 A | 9/2000 | Rehfuss et al. |
| 6,117,024 A | 9/2000 | Dewanjee |
| 6,117,843 A | 9/2000 | Baroody et al. |
| 6,123,963 A | 9/2000 | Kim et al. |
| 6,126,958 A | 10/2000 | Saleh et al. |
| 6,130,200 A | 10/2000 | Brodbeck et al. |
| 6,130,309 A | 10/2000 | Reich et al. |
| 6,140,453 A | 10/2000 | Julia Barges et al. |
| 6,150,489 A | 11/2000 | Pudleiner et al. |
| 6,160,058 A | 12/2000 | Ohrbom et al. |
| 6,184,248 B1 | 2/2001 | Lee et al. |
| 6,187,756 B1 | 2/2001 | Lee et al. |
| 6,188,039 B1 | 2/2001 | Gass |
| 6,197,327 B1 | 3/2001 | Harrison et al. |
| 6,210,343 B1 | 4/2001 | Kanakaris et al. |
| 6,210,441 B1 | 4/2001 | Flodin |
| 6,221,997 B1 | 4/2001 | Woodhouse et al. |
| 6,284,836 B1 | 9/2001 | Hassel et al. |
| 6,294,550 B1 | 9/2001 | Place et al. |
| 6,303,147 B1 | 10/2001 | Gilis |
| 6,303,606 B1 | 10/2001 | Leonardi et al. |
| 6,306,841 B1 | 10/2001 | Place et al. |

| Patent No. | Date | Inventor(s) | Pub. No. | Date | Inventor(s) |
|---|---|---|---|---|---|
| 6,323,241 B1 | 11/2001 | Yeager et al. | 2002/0119833 A1 | 8/2002 | Dewanjee |
| 6,328,991 B1 | 12/2001 | Myhling | 2002/0128314 A1 | 9/2002 | Neal |
| 6,335,003 B1 | 1/2002 | Kim et al. | 2002/0132965 A1 | 9/2002 | Gertzmann et al. |
| 6,346,599 B1 | 2/2002 | Goldberg et al. | 2002/0161009 A1 | 10/2002 | Leonardi et al. |
| 6,359,100 B1 | 3/2002 | Hostettler et al. | 2003/0022022 A1 | 1/2003 | Kizumoto et al. |
| 6,403,665 B1 | 6/2002 | Sieker et al. | 2003/0032754 A1 | 2/2003 | Kaufhold et al. |
| 6,410,595 B1 | 6/2002 | Neal | 2003/0032759 A1 | 2/2003 | Fischer et al. |
| 6,413,536 B1 | 7/2002 | Gibson et al. | 2003/0045668 A1 | 3/2003 | Fischer et al. |
| 6,414,027 B1 | 7/2002 | Neal | 2003/0060589 A1 | 3/2003 | Shimizu et al. |
| 6,414,028 B1 | 7/2002 | Buyuktimkin et al. | 2003/0122282 A1 | 7/2003 | Plummer et al. |
| 6,416,779 B1 | 7/2002 | O'Augustine et al. | 2003/0129241 A1 | 7/2003 | Yeager et al. |
| 6,420,510 B1 | 7/2002 | Kaufhold et al. | 2003/0134903 A1 | 7/2003 | Yeager et al. |
| 6,423,788 B1 | 7/2002 | Bammel et al. | 2003/0144454 A1 | 7/2003 | Krebs et al. |
| 6,440,568 B1 | 8/2002 | Kayanoki et al. | 2003/0158369 A1 | 8/2003 | Slagel |
| 6,469,016 B1 | 10/2002 | Place et al. | 2003/0207852 A1 | 11/2003 | Place et al. |
| 6,469,055 B2 | 10/2002 | Lee et al. | 2003/0212139 A1 | 11/2003 | Neal |
| 6,471,955 B1 | 10/2002 | Tremont et al. | 2004/0014761 A1 | 1/2004 | Place et al. |
| 6,472,434 B1 | 10/2002 | Place et al. | 2004/0044080 A1 | 3/2004 | Place et al. |
| 6,482,345 B1 | 11/2002 | Dewanjee | 2004/0047910 A1 | 5/2004 | Beckett et al. |
| 6,486,207 B2 | 11/2002 | Yeager et al. | 2004/0110843 A1 | 6/2004 | Yeager et al. |
| 6,488,953 B2 | 12/2002 | Halliday et al. | 2004/0115229 A1 | 6/2004 | Roby |
| 6,495,157 B1 | 12/2002 | Pena et al. | 2004/0131664 A1 | 7/2004 | Mo et al. |
| 6,511,388 B1 | 1/2003 | Dewanjee | 2004/0142847 A1 | 7/2004 | Bayersdoerfer et al. |
| 6,512,073 B2 | 1/2003 | Gertzmann et al. | 2004/0157766 A1 | 8/2004 | Embil et al. |
| 6,521,164 B1 | 2/2003 | Plummer et al. | 2004/0265355 A1 | 12/2004 | Shalaby |
| 6,537,970 B1 | 3/2003 | Vulpescu et al. | 2004/0266688 A1 | 12/2004 | Nayak |
| 6,543,828 B1 | 4/2003 | Gass | 2005/0004226 A1 | 1/2005 | Lu et al. |
| 6,545,119 B2 | 4/2003 | Kizumoto et al. | 2005/0013793 A1 | 1/2005 | Beckman et al. |
| 6,559,184 B2 | 5/2003 | Neal | 2005/0031690 A1 | 2/2005 | Rohrs et al. |
| 6,572,874 B1 | 6/2003 | Harrison et al. | 2005/0048104 A1 | 3/2005 | Venkatraman et al. |
| 6,586,553 B1 | 7/2003 | Muhlfeld et al. | 2005/0053639 A1 | 3/2005 | Shalaby |
| 6,589,990 B1 | 7/2003 | Kanakaris et al. | 2005/0053670 A1 | 3/2005 | Schaub |
| 6,592,472 B2 | 7/2003 | Dewanjee | 2005/0070516 A1 | 3/2005 | Wilson et al. |
| 6,593,313 B2 | 7/2003 | Place et al. | 2005/0090474 A1 | 4/2005 | Naor |
| 6,593,369 B2 | 7/2003 | Neal | 2005/0095245 A1 | 5/2005 | Riley et al. |
| 6,607,686 B2 | 8/2003 | Dewanjee | 2005/0161030 A1 | 7/2005 | Robert et al. |
| 6,630,050 B1 * | 10/2003 | Moeller et al. ............. 156/331.7 | 2005/0169975 A1 | 8/2005 | Suzuki et al. |
| 6,632,913 B2 | 10/2003 | Matsumoto et al. | 2005/0181030 A1 | 8/2005 | Mo et al. |
| 6,641,064 B1 | 11/2003 | Dentler et al. | 2005/0187342 A1 | 8/2005 | Schieferstein et al. |
| 6,642,274 B1 | 11/2003 | Neal | 2005/0208152 A1 | 9/2005 | Milankovits |
| 6,664,290 B1 | 12/2003 | El-Rafaey | 2005/0238722 A1 | 10/2005 | Pathak et al. |
| 6,693,135 B2 | 2/2004 | Yeager et al. | 2005/0245902 A1 | 11/2005 | Cornish et al. |
| 6,740,333 B2 | 5/2004 | Beckett et al. | 2006/0003950 A1 | 1/2006 | Strugnell et al. |
| 6,790,926 B1 | 9/2004 | Spijkers et al. | 2006/0018951 A1 | 1/2006 | Maniar et al. |
| 6,794,372 B2 | 9/2004 | Del Soldato et al. | 2006/0041021 A1 | 2/2006 | Wilson et al. |
| 6,825,234 B2 | 11/2004 | Yeager et al. | 2006/0052341 A1 | 3/2006 | Cornish et al. |
| 6,841,574 B2 | 1/2005 | Mo et al. | 2006/0078616 A1 | 4/2006 | Georgewill et al. |
| 6,861,503 B2 | 3/2005 | Shalaby | 2006/0093675 A1 | 5/2006 | Ebmeier et al. |
| 6,953,800 B2 | 10/2005 | Leonardi et al. | 2006/0134161 A1 | 6/2006 | Halliday |
| 6,992,161 B1 | 1/2006 | Kim et al. | 2006/0183724 A1 | 8/2006 | Diliberti et al. |
| 7,053,209 B1 | 5/2006 | Gibson et al. | 2006/0210599 A1 | 9/2006 | Gibson et al. |
| 7,179,481 B2 | 2/2007 | Villanueva | 2007/0043332 A1 | 2/2007 | Malcolm et al. |
| 7,485,666 B2 | 2/2009 | Villanueva et al. | 2007/0128154 A1 | 6/2007 | Hadba et al. |
| 7,670,606 B2 | 3/2010 | Volkmann | 2007/0135605 A1 | 6/2007 | Hadba et al. |
| 7,717,892 B2 | 5/2010 | Bartning | 2007/0148105 A1 | 6/2007 | Spector |
| 7,795,467 B1 | 9/2010 | Pacetti et al. | 2007/0155906 A1 | 7/2007 | Hissink et al. |
| 7,829,112 B2 | 11/2010 | Ron et al. | 2007/0166382 A1 | 7/2007 | Kiser et al. |
| 7,833,543 B2 | 11/2010 | Gibson et al. | 2007/0282093 A1 | 12/2007 | Yoshimura et al. |
| 7,833,545 B2 | 11/2010 | Ron et al. | 2008/0009663 A1 | 1/2008 | Bartning et al. |
| 7,838,024 B2 | 11/2010 | Ron et al. | 2008/0009666 A1 | 1/2008 | Bartning et al. |
| 7,883,718 B2 | 2/2011 | Ron et al. | 2008/0108775 A1 | 5/2008 | Schieferstein et al. |
| 7,892,163 B2 | 2/2011 | Bartning et al. | 2008/0140185 A1 | 6/2008 | Kiser et al. |
| 2001/0014715 A1 | 8/2001 | Blum et al. | 2008/0145419 A1 | 6/2008 | Gibson et al. |
| 2001/0044467 A1 | 11/2001 | Neal | 2008/0152708 A1 | 6/2008 | Gibson et al. |
| 2001/0051656 A1 | 12/2001 | Place et al. | 2008/0199511 A1 | 8/2008 | Sitruk-Ware et al. |
| 2001/0051694 A1 | 12/2001 | Julia Barges et al. | 2008/0206310 A1 | 8/2008 | Davis |
| 2002/0004529 A1 | 1/2002 | Neal | 2008/0207571 A1 | 8/2008 | Davis |
| 2002/0013304 A1 | 1/2002 | Wilson et al. | 2008/0262613 A1 | 10/2008 | Gogolewski |
| 2002/0028846 A1 | 3/2002 | Yeager et al. | 2008/0271190 A1 | 10/2008 | Holland |
| 2002/0037491 A1 | 3/2002 | Halliday et al. | 2008/0286339 A1 | 11/2008 | Ron et al. |
| 2002/0039935 A1 | 4/2002 | Dewanjee | 2009/0004246 A1 | 1/2009 | Woolfson et al. |
| 2002/0045665 A1 | 4/2002 | Yeager et al. | 2009/0011209 A1 | 1/2009 | Steinberger et al. |
| 2002/0052407 A1 | 5/2002 | Lee et al. | 2009/0060982 A1 | 3/2009 | Ron et al. |
| 2002/0062097 A1 | 5/2002 | Simpson | 2009/0061172 A1 | 3/2009 | Hayashi et al. |
| 2002/0077442 A1 | 6/2002 | Gertzmann et al. | 2009/0081278 A1 | 3/2009 | De Graaff et al. |
| 2002/0077444 A1 | 6/2002 | Matsumoto et al. | 2009/0203591 A1 | 8/2009 | Bagchi et al. |
| 2002/0099003 A1 | 7/2002 | Wilson et al. | 2009/0203772 A1 | 8/2009 | Villanueva et al. |
| 2002/0115814 A1 | 8/2002 | Woodhouse et al. | 2009/0291120 A1 | 11/2009 | Tuominen et al. |
| 2002/0115976 A1 | 8/2002 | Fleming | 2010/0104619 A1 | 4/2010 | De Graaff et al. |

| | | | |
|---|---|---|---|
| 2010/0203104 A1 | 8/2010 | De Graaff et al. | |
| 2010/0285094 A1 | 11/2010 | Gupta | |
| 2011/0045076 A1 | 2/2011 | Kiser et al. | |
| 2011/0056501 A1 | 3/2011 | Kortesuo et al. | |
| 2011/0059040 A1 | 3/2011 | Kiser et al. | |
| 2011/0077578 A1 | 3/2011 | Bartning et al. | |
| 2011/0091488 A1 | 4/2011 | Halliday et al. | |
| 2011/0150955 A1 | 6/2011 | Klingman | |

FOREIGN PATENT DOCUMENTS

| | | |
|---|---|---|
| EP | 335669 | 3/1989 |
| EP | 0401990 | 5/1990 |
| EP | 424164 | 10/1990 |
| EP | 0401990 | 12/1990 |
| EP | 0450176 | 10/1991 |
| EP | 1063942 | 6/2004 |
| FR | 2557576 | 7/1985 |
| FR | 2557576 | 7/1986 |
| FR | 2705567 | 12/1994 |
| GB | 2047093 | 11/1980 |
| GB | 2047094 | 11/1980 |
| GB | 2244920 | 12/1991 |
| JP | 56500253 | 3/1980 |
| JP | 1135488 | 9/1989 |
| JP | 1150610 | 10/1989 |
| JP | 0670952 | 3/1994 |
| JP | 200502691 | 3/2000 |
| JP | 2001513550 | 9/2001 |
| JP | 2002515069 | 5/2002 |
| JP | 2011507405 | 3/2011 |
| WO | WO 80/01984 | 10/1980 |
| WO | 89/05319 | 6/1989 |
| WO | 89/07117 | 8/1989 |
| WO | 91/02763 | 3/1991 |
| WO | 94/03510 | 2/1994 |
| WO | 94/13724 | 6/1994 |
| WO | 94/22934 | 10/1994 |
| WO | 96/06875 | 3/1996 |
| WO | 96/15171 | 5/1996 |
| WO | 96/21427 | 7/1996 |
| WO | 96/31551 | 10/1996 |
| WO | WO 96/38153 | 12/1996 |
| WO | 97/17386 | 5/1997 |
| WO | 97/24109 | 7/1997 |
| WO | WO 97/24109 | 7/1997 |
| WO | WO 98/56323 | 12/1998 |
| WO | WO 99/09964 | 3/1999 |
| WO | 99/47073 | 9/1999 |
| WO | 99/47127 | 9/1999 |
| WO | 99/56731 | 11/1999 |
| WO | 00/00222 | 1/2000 |
| WO | 00/40222 | 7/2000 |
| WO | WO 00/40222 | 7/2000 |
| WO | WO 02/03896 | 1/2002 |
| WO | WO 02/09631 | 2/2002 |
| WO | 2003/011301 | 2/2003 |
| WO | 03/087183 | 10/2003 |
| WO | 2004/029125 | 4/2004 |
| WO | 2004/084872 | 10/2004 |
| WO | 2005/116100 | 2/2005 |
| WO | 2005/068533 | 7/2005 |
| WO | WO 2005/063145 | 7/2005 |
| WO | 2005/089778 | 9/2005 |
| WO | 2006/013335 | 2/2006 |
| WO | 2006/048639 | 5/2006 |
| WO | 2006/048639 | 11/2006 |
| WO | 2008/007098 | 1/2008 |
| WO | 2009/094573 | 7/2009 |
| WO | WO 2010/035837 | 4/2010 |
| WO | WO 2010/119029 | 5/2010 |
| WO | WO 2011/011099 | 1/2011 |
| WO | WO 2011/039418 | 4/2011 |

OTHER PUBLICATIONS

Santerre, et al., "Understanding the biodegradation of polyurethanes: From classical implants to tissue engineering materials." Biomaterials 26(35), Dec. 2005: 7457-7470.

Leiva, et al., "Poly(£-caprolactone)-block-poly(ethylene-oxide) -block-poly(£-V caprolactone): Biodegradable triblock copolymer spread at the air-water interface." European Polymer Journal 44(8), Aug. 2008: 2589-2598.

Zhou, et al., "Biodegradable poly(e-caprolactone)-poly(ethylene glycol) block copolymers: characterization and their use as drug carriers for a controlled delivery system." Biomaterials (2003) 24(20): 3563-3570.

Jianzhong, et al., "Polycaprolactone-poly(ethylene glycol) block copolymer III Drug release behavior." Chinese J Polym Sci., 13(2) 1995: 154:161.

Lee JW, et al., "Thermoreversible gelation of biodegradable poly(epsilon-caprolactone) and poly(ethylene glycol) multiblock copolymers in aqueous solutions." J Control Release. Jun. 15, 2001; 73(2-3): 315-27.

Abraham, et al., "Bioresorbable poly(ester-ether urethane)s from L-lysine diisocyanate and triblock copolymers with different hydrophilic character." Journal of Biomedical Materials Research Part A (2006) 76(4): 729-736.

Baimak, et al., "Synthesis and characterization of poly(I-lactide-co-e-caprolactone) copolymers: Effect of stannous octoate initiator and diethylel glycol coinitiator concentration." Science Asia 30 (2004): 324-334.

Castenada, C.S., et al. "Misoprostol Dose Selection in a Controlled-Release Vaginal Insert for Induction of Labor in Nulliparous Women," American Journal of Obstetrics and Gynecology, 193:1071-1075, (Sep. 2005).

Tyagi, P., et al., "Sustained Intravesical Drug Delivery Using Thermosensitive Hydrogel," Pharmaceutical Research, 21 (5):832-837 (May 2004).

Abraham, Gustavo A., et al. "Bioresorbable poly(ester-ether urethane)s from L-lysine diisocyanate and triblock copolymers with different hydrophilic character," Wiley Periodicals 2005.

PCT/GB2007/002401 International Search Report dated Oct. 24, 2007.

PCT/GB2007/002401 Written Opinion of the International Searching Authority dated Oct. 24, 2007.

PCT/GB2007/002415 International Search Report dated Oct. 30, 2007.

PCT/GB2007/002415 Written Opinion of the International Searching Authority dated Oct. 30, 2007.

Yu, J., et al. "Blood interactions with novel polyurethaneurea hydrogels," Biomaterials 12(2): 119-120 (1991).

PCT/GB2005/002951 Written Opinion of the International Searching Authority dated Oct. 6, 2005.

PCT/GB2005/002951 International Preliminary Report on Patentability dated Feb. 6, 2007.

PCT/GB2005/002951 International Search Report dated Oct. 20, 2005.

PCT/GB2003/004208 International Search Report dated Jan. 2, 2004.

PCTGB207 002604 International Search Report Jul. 12, 2007.

PCTGB207 002604 Written Opinion of International Searching Authority Jul. 12, 2007.

Chen, "Stabilization and sustained-release effect of Misoprostol with Methacrylate copolymer", International Journal of Pharmaceutics, 203 (2000) pp. 141-148.

Kararli, "Stabilization of Misoprostol with Hydroxypropyl Methylcellulose (HMPC) Against Degradation by Water", Pharmaceutical Research, vol. 7, No. 11 (1990).

PCT/GB207/002604, International Search Report, dated Jul. 12, 2007.

* cited by examiner

Figure 1. Molecular weight analysis as a function of polymerization time for Polymers B and C.
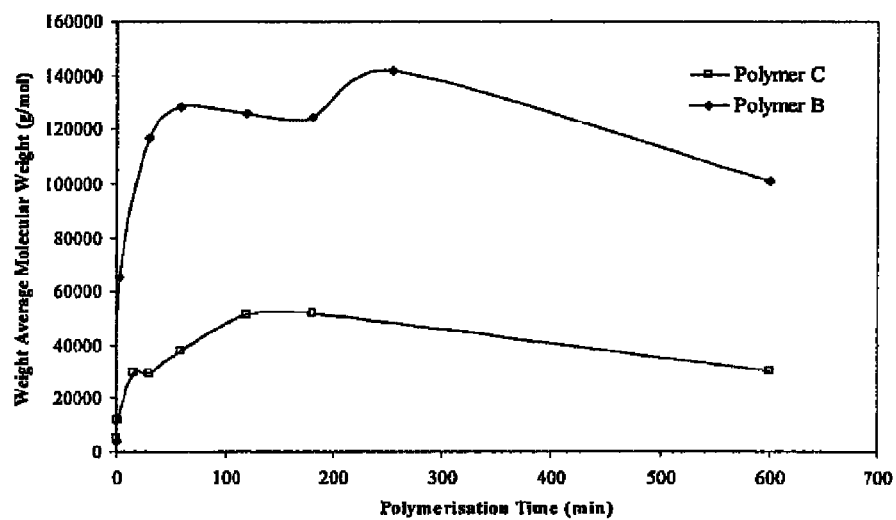
Figure 2a. Fluconazole release from Polymers A and C
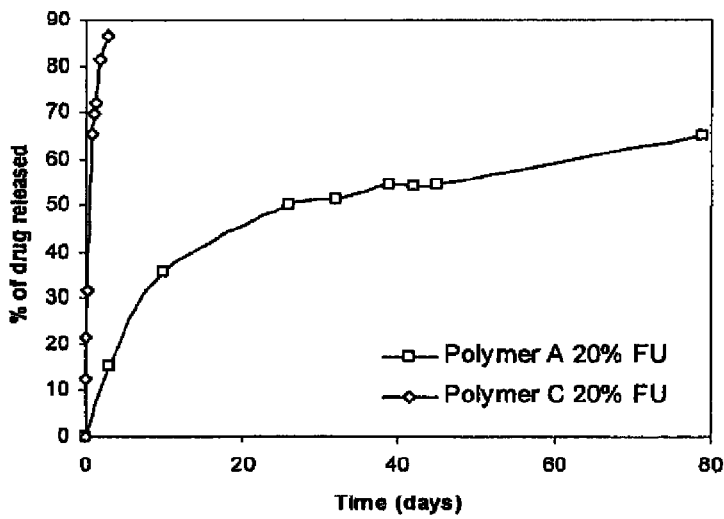

Figure 2b. Oxybutynin release from polymers Polymers A, B and C.
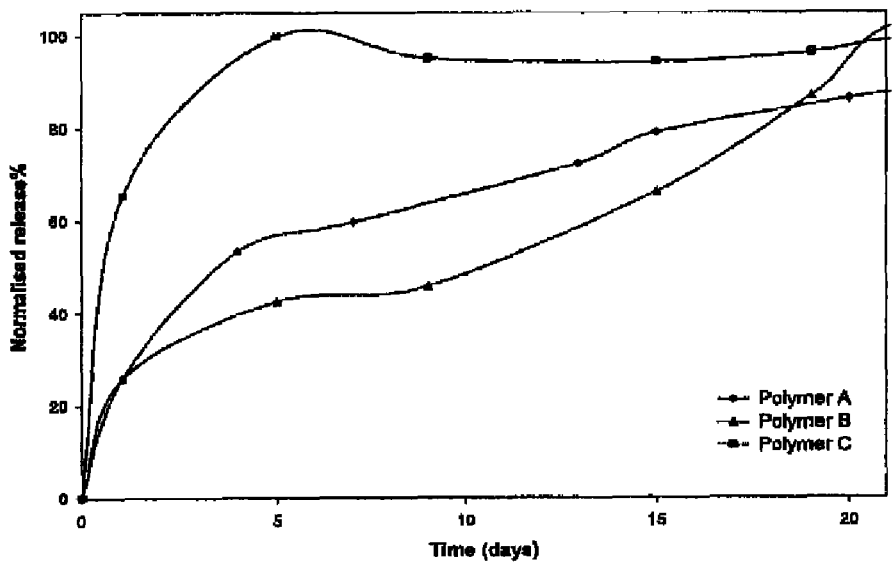
Figure 3. Release profiles obtained for Polymer A when fluconazole at 20wt% and oxybutynin at 15wt% were loaded.
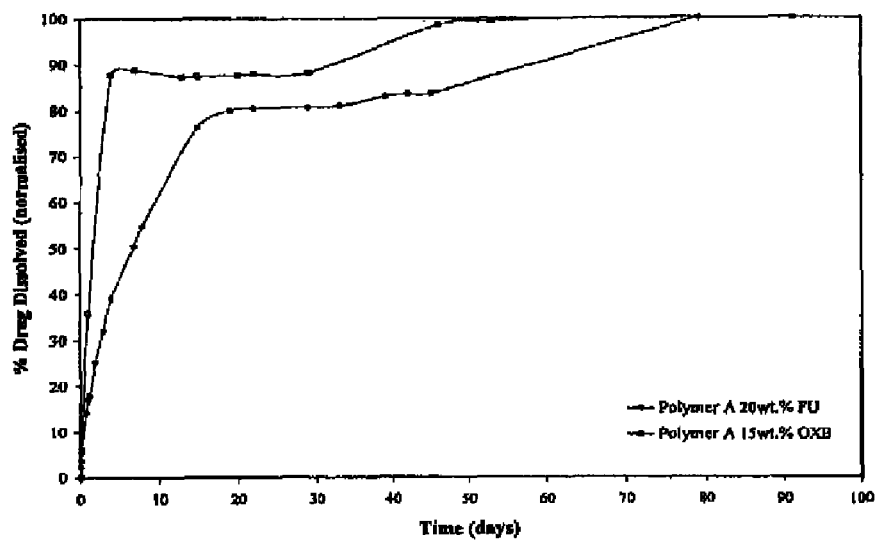

Figure 4. Release profiles obtained for Polymer A at 20wt% and 50wt% of fluconazole.
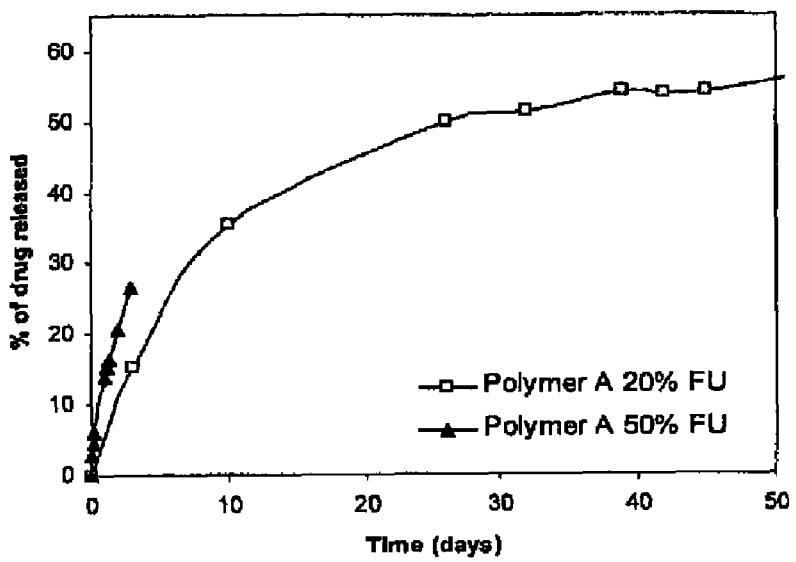
Figure 5. Comparison of the fluconazole release profiles from the crosslinked polymer, linear high-swelling polymers, Polymer A and Polymer C.
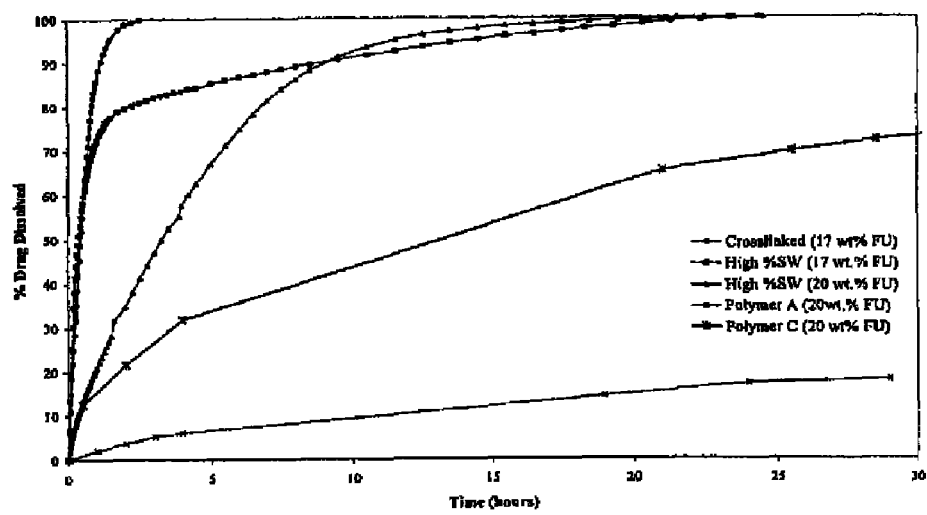

POLYURETHANE ELASTOMERS

CROSS-REFERENCE TO RELATED APPLICATIONS

This application is a continuation of U.S. application Ser. No. 12/373,002, filed Jul. 2, 2009, which is a National Stage filing under 35 U.S.C. §371 of International Application No. PCT/GB2007/002415, filed Jun. 27, 2007, which claims priority from United Kingdom Patent Application No. 0613638.6, filed Jul. 8, 2006. The contents of the foregoing applications are herein incorporated by reference.

TECHNICAL FIELD

The present invention relates to hydrophilic thermoplastic polyurethane elastomer polymers, suitable for the production of controlled release compositions for release of pharmaceutically active agents over a prolonged period of time. Their elastomeric nature provides better comfort in use, for example, in pessaries, suppositories or vaginal rings.

BACKGROUND

Certain cross-linked polyurethane hydrogel polymers are known from European Patent Publications EP0016652 and EP0016654. These patent specifications describe cross-linked polyurethanes formed by reacting a polyethylene oxide of equivalent weight greater than 1500 with a polyfunctional isocyanate and a trifunctional compound reactive therewith, such as an alkane triol. The resultant cross-linked polyurethane polymers are water-swellable to form a hydrogel but are water-insoluble and may be loaded with water-soluble pharmaceutically active agents. One particular polyurethane polymer is the reaction product of polyethylene glycol 8000, Desmodur (DMDI i.e. dicyclohexylmethane-4,4-diisocyanate) and 1,2,6-hexane triol and which has been used commercially for vaginal delivery of prostaglandins.

However, such polyurethane polymers possess a number of practical disadvantages. Whilst the use of a triol cross-linking agent is effective in providing polymers of relatively reproducible swelling characteristics, the percent swelling is typically 200-300% (i.e. the increase in weight of the swollen polymer divided by the weight of the dry polymer). Pharmaceutically active agents are loaded by contacting the polymer with an aqueous solution of pharmaceutically active agent, such that the solution becomes absorbed into the polymer, forming a hydrogel. The swollen polymer is then dried back to the chosen water content before use. A consequence is that with the conventional cross-linked polyurethane, the degree of swelling limits the molecular weight of the pharmaceutically active agent which can be absorbed into the hydrogel structure to below about 3000 g/mol. A further disadvantage is that only water-soluble pharmaceutically active agents may be used. Finally, since the conventional cross-linked polyurethane polymer is essentially a non-thermoplastic polymer (thermoset), insoluble in both water and organic solvents, the further processing of the formed polymer into other solid forms, such as films, monolithic devices, foams, wafers, composites, sandwich structures, particles, pellets, foams or coatings, is not possible. In addition, the thermoset nature of the conventional cross-linked polyurethane polymer rules out the possibility of melt mixing drug with the polymer, in order to load the polymer with a suitable active agent without using solvents or water.

Certain thermoplastic polyurethane hydrogel polymers are known from patent Publication WO2004029125. This patent specification describes linear thermoplastic polyurethanes formed by reacting a polyethylene glycol of molecular weight of greater than 4000 g/mol with a polyfunctional isocyanate and a bifunctional compound reactive therewith, such as an alkane diol or diamine. The resultant thermoplastic polyurethane polymers are water-swellable to form a hydrogel but are water-insoluble and may be loaded with water-soluble pharmaceutically active agents. One particular polyurethane polymer is the reaction product of polyethylene glycol 8000, Desmodur (DMDI, i.e., dicyclohexylmethane-4,4-diisocyanate) and 1,10-decane diol, which has shown percentage-swelling from 600% up to 1700% or even above. This type of polymer has shown a suitability for diffusion loading and short-term delivery of relatively water-soluble drugs e.g. clindamycin phosphate, oxytocin, and misoprostol.

However, such a high-swelling thermoplastic polyurethane polymer possesses many practical disadvantages. Due to the high weight content and block length of PEG, the polymer is only suitable for relatively short-term release (i.e. controlled release from 10 min to only a few hours) of active agents, especially in the case of highly water-soluble drugs. In addition, the low hydrophobic content, i.e. low amount of hydrophobic compound e.g. decanediol (DD) or dodecanediol (DDD) makes the polymer inappropriate for hydrophobic drugs and thus restricts its use. Hydrophilic and hydrophobic drugs need to have interactions with both of the phases in order for their release to be controlled by the polymer structure. Further, the imbalance between hydrophobic and hydrophilic compounds hampers microphase separation, which reduces the mechanical strength of the polymer in both the dry and wet state. In addition, due to the high crystallinity of polymer and the formation of hard blocks, the final polymer is rigid and the processing temperature relatively high.

The swelling percentage of high-swelling thermoplastic polyurethanes is typically 200-1700% and is dependent on the PEG content and/or the length of PEG block. Pharmaceutically active agents can be loaded by using the same method as described above for the conventional cross-linked polyurethane, as well as melt mixing drug and polymer. The release time and profiles obtained for the high swelling and crosslinked polyurethane polymers are, however, very similar.

Patent specification WO 94/22934 discloses the production of a linear random block copolymer from polyethylene oxide (number average molecular weight 1000 to 12,000), a diamine and a diisocyanate. Yu et al. Biomaterials 12 (1991) March, No. 2, page 119-120 discloses the use of polyurethane hydrogels formed of polyethylene glycol (number average molecular weight of 5830) and a low molecular weight polypropylene glycol (molecular weight 425) and a diisocyanate. Patent specification U.S. Pat. No. 4,202,880 discloses the production of polyurethanes from polyethylene glycol (molecular weight 400-20,000), an alkaline glycol containing from 2-6 carbon atoms and a diisocyanate. Patent specification U.S. Pat. No. 4,235,988 is a similar disclosure, although the preferred PEG range is 600-6,000.

BRIEF DESCRIPTION OF DRAWINGS

FIG. 1 shows molecular weight as a function of polymerisation time for certain polymers; and FIGS. 2 to 5 show various active agent release profiles.

DETAILED DESCRIPTION

The object of the present invention is to provide a hydrophilic thermoplastic polyurethane elastomer, which can be processed and mixed with an active agent at the temperature below the degradation temperature of the active agent by using conventional polymer processing systems, e.g. melt mixer, extruder and injection moulding machine. An additional objective of the present invention is to enhance the melt viscosity, to increase elasticity and to lower the crystallinity of the polymer in order to apply conventional melt processing techniques e.g. extrusion and injection moulding, as well as different types of solvents to the formation of drug loaded resilient controlled release devices of any chosen shape.

The present invention is based on the discovery that thermoplastic polyurethane elastomers having suitable melt processing properties for drug loading and elasticity at body temperature, as well as suitable drug release characteristics, may be obtained by reacting a polyethylene glycol or polypropylene glycol with a diol or other difunctional compound, and a PPG-PEG-PPG or PEG-PPG-PEG block copolymer and a difunctional isocyanate.

PEG stands for polyethylene glycol; and PPG stands for polypropylene glycol.

In particular, the present invention provides a hydrophilic thermoplastic polyurethane elastomer polymer obtainable by reacting together:
  (a) a polyethylene glycol or polypropylene glycol;
  (b) a PEG-PPG-PEG or PPG-PEG-PPG block copolymer;
  (c) a difunctional compound; and
  (d) a difunctional isocyanate.

The thermoplastic polyurethane elastomer produced is swellable in water to a specific degree, depending upon the ratio of the four components (a), (b), (c) and (d), for example from 1% up to 200% (e.g. 20 to 100%) thus better controlling the release of pharmaceutically active agents from the high-swelling, PEG-based linear polyurethane. The polymer of the invention is also soluble in certain organic solvents, such as dichloromethane, 1-methyl-2-pyrrolidone (NMP) and tetrahydrofuran, which allows the polymer to be dissolved and cast into films or coatings. It also allows thermally unstable active agents of poor water solubility but which are soluble in organic solvents, to be loaded into the polymer.

Due to the unique combination of starting components, these polyurethane elastomers have a composition that can control the release of active compounds from a few days up to a few months.

Polyether polyols contain the repeating ether linkage —R—O—R— and have two or more hydroxyl groups as terminal functional groups. They are manufactured by the catalysed addition of epoxides to an initiator (anionic ring-opening polymerisation). The most important of the cyclic ethers by far are ethylene oxide and propylene oxide. These oxides react with active hydrogen-containing compounds (initiators), such as water, glycols, polyols and amines. A catalyst may or may not be used. Potassium hydroxide or sodium hydroxide is the basic catalyst most often employed. After the desired degree of polymerisation has been achieved, the catalyst is neutralized, removed by filtration and additives such as antioxidants are added.

A wide variety of compositions of varying structures, chain lengths and molecular weights is possible. By selecting the oxide or oxides, initiator, and reaction conditions and catalysts, it is possible to polymerise a series of polyether polyols that range from low-molecular-weight polyglycols to high-molecular-weight polymers. Since these polymers contain repeating alkylene oxide units, they are often referred to as polyalkylene glycols or polyglycols. Most polyether polyols are produced for polyurethane applications.

Polyethylene glycols (PEG) contain the repeat unit (—$CH_2CH_2O$—) and are conveniently prepared by the addition of ethylene oxide to ethylene glycol to produce a difunctional polyethylene glycol structure HO($CH_2CH_2O$)$_n$H wherein n is an integer of varying size depending on the molecular weight of the polyethylene glycol. Polyethylene glycols used in the present invention are generally linear polyethylene glycols i.e. diols having molecular weights of 200 to 35,000 g/mol. (generally 400 to 2000).

Polypropylene glycols (PPG) are polymers of propylene oxide and thus contain the repeat unit (—$CH_2(CH_3)$ $CH_2O$—). Polypropylene glycol has unique physical and chemical properties due to the co-occurrence of both primary and secondary hydroxyl groups during polymerisation, and to the multiplicity of methyl side chains on the polymers. Conventional polymerisation of propylene glycol results in an atactic polymer. The isotactic polymers mainly exist in the laboratory. Mixtures of atactic and isotactic polymers may also occur. PPG has many properties in common with polyethylene glycol. Polypropylene glycols of all molecular weights are clear, viscous liquids with a low pour point, and which show an inverse temperature-solubility relationship, along with a rapid decrease in water solubility as the molecular weight increases. The terminal hydroxyl groups undergo the typical reactions of primary and secondary alcohols. The secondary hydroxyl group of polypropylene glycols is not as reactive as the primary hydroxyl group in polyethylene glycols. PPG is used in many formulations for polyurethanes. Polypropylene glycols used in the present invention are generally linear having molecular weights of 200 to 4000 g/mol, (generally 400 to 2000).

The invention also provides a method of producing the linear polymer, which comprises melting and drying PEG or PPG, and the block copolymer, together with the difunctional compound at a temperature of 85° C. to 100° C. under vacuum; and then adding the difunctional isocyanate.

The production of block copolymers (b), based on propylene oxide and ethylene oxide, can be initiated with ethylene glycol, glycerine, trimethylolethane, trimethylolpropane, pentaerythritol, sorbitol, sucrose and several other compounds. Mixed and alternating block copolymers can also be produced. When the secondary hydroxyl groups of PPG are capped with ethylene oxides, block copolymers of PEG and PPG with terminal primary hydroxyl groups are yield. The primary hydroxyl groups are more reactive with isocyanates than secondary hydroxyl groups. PEG-PPG-PEG and PPG-PEG-PPG copolymers used in the present invention are generally linear having molecular weight of 200 to 14,000 g/mol. The block copolymer appears to contribute to the non-crystalline elastomeric nature of the polymer of the invention.

The difunctional compound (c) is reactive with the difunctional isocyanate, and is typically a difunctional amine or diol. Diols in the range $C_5$ to $C_{20}$, preferably $C_8$ to $C_{15}$ are preferred. Thus, decanediol has been found to produce particularly good results. The diol may be a saturated or unsaturated diol. Branched diols may be used but straight chain diols are preferred. The two hydroxyl groups are generally on terminal carbon atoms. Preferred diols include 1,6-hexanediol, 1,10-decanediol, 1,12-dodecanediol and 1,16-hexadecanediol.

The difunctional isocyanate (d) is generally one of the conventional diisocyanates, such as dicyclohexylmethane-4,4-diisocyanate, diphenylmethane-4,4-diisocyanate, 1,6-hexamethylene diisocyanate etc.

The equivalent weight ratio of the components (a), (b), (c) and (d) is generally in the range 0.01-1 to 0.01-1 to 1 to 1.02-3 respectively. Of course, the skilled man through reasonable experimentation would determine the best ratio of ingredients to give the desired properties. The amount of component (d)

is generally equal to the combined amounts of (a), (b) and (c) to provide the correct stoichiometry.

The polymers are generally produced by melting and drying PEG or PPG, and PEG-PPG-PEG or PPG-PEG-PPG block copolymer together with the difunctional compound and a typical polyurethane catalyst (if used), e.g. ferric chloride, DABCO and/or tin (II) octoate, at a temperature of 85° C. to 100° C. (e.g. 95° C.) under vacuum to remove excess moisture; before the diisocyanate, e.g. DMDI or HMDI is added thereto. The polymerisation is carried out in a batch or alternatively a continuous reactor; or the reaction mixture is fed into moulds and reacted for a specified time. After polymerisation the polymer is cooled down, pelletised or granulated and stored in a freezer for further analysis and processing.

The elastomeric properties of the thermoplastic polyurethane elastomers of the invention are due to two factors: microphase separation of hard and soft blocks; and the semicrystalline nature of the polymer, whose amorphous phase has a low glass transition temperature. Hard blocks form from the difunctional compound and diisocyanate. Soft blocks are PEG, PPG or copolymer. The elasticity may depend on the ratio of hard to soft blocks and may be represented by Shore hardness measurements.

The linear polymers of the present invention are soluble in certain organic solvents. This allows the polymer to be dissolved and the resultant solution cast to form films. The solution may also be employed for coating granules, tablets etc., in order to modify the polymer release properties. Alternatively, the solution can be poured into a non-solvent so as to precipitate polymer/active microparticles. In addition, the polymer can be ground, chopped, pelletised and melted by using conventional techniques used for processing thermoplastic polymers.

Thus, the invention also provides a controlled release composition comprising the linear polymer together with an active agent. Any type of plastic processing equipment, e.g. extruder, injection moulding machine, compression moulding equipment and melt mixer can be used for mixing the polymer and active agent together and forming or reshape into any type of drug loaded device, e.g. a ring, pessary, patch, rod, spring or cone. The active agent may be a pharmaceutically active agent for human or animal use. It may also be any other agent where sustained release properties (e.g. algicides, fertilisers etc.) are required. The pharmaceutical solid dosage forms include suppositories, rings and pessaries for vaginal use, buccal inserts for oral administration, patches for transdermal administration etc. These dosage forms are generally administered to the patient, retained in place until delivery of active agent has occurred and the spent polymer is then removed. The polymer may also be used for implants, which remain in the body; or for coating such implants (e.g. stents).

The polymer of the present invention is an amphiphilic thermoplastic polymer and is thus suitable for the uptake of hydrophilic and hydrophobic, low and high molecular weight pharmaceutically active agents (up to and exceeding a molecular weight of 3000 e.g. up to 10,000, up to 50,000, up to 100,000 or even up to 200,000). Generally, the molecular weight of the active agent is in the range 200 to 20,000. A wide variety of water-soluble pharmaceutically active substances such as those listed in EP0016652 may thus be incorporated. Furthermore, the linear polymers of the present invention may be loaded with pharmaceutically active hydrophilic and hydrophobic agents, which are poorly water-soluble, provided that these can be dissolved in a common solvent with the polymer. The resultant solution can then be cast into any desired solid form. In addition, the linear polymers of the present invention may be extrusion loaded or melt mixed with pharmaceutically active agents, which are thermally stable at the polymer processing temperature.

The release time of the present polymers may exceed 12 hrs, 24 hrs, 5 days, 10 days, 20 days or even 80 days for substantially complete release of available active agent.

The polyether polyol blends and copolymers used in the present invention are internal and melt rheology, softness and release rate modifiers. These types of low melting amphiphilic thermoplastic polyurethane polymers are particularly suitable for the melt loading of pharmaceutically active agent and melt processing of loaded polymer to pharmaceutical devices.

Pharmaceutically active agents of particular interest include: proteins e.g. interferon alpha, beta and gamma, insulin, human growth hormone, leuprolide; benzodiazepines e.g. midazolam; anti-migraine agents e.g. triptophans, ergotamine and its derivatives; anti-infective agents e.g. azoles, bacterial vaginosis, candida; and ophthalmic agents e.g. latanoprost.

A detailed list of active agent includes $H_2$ receptor antagonist, antimuscaririe, prostaglandin analogue, proton pump inhibitor, aminosalycilate, corticosteroid, chelating agent, cardiac glycoside, phosphodiesterase inhibitor, thiazide, diuretic, carbonic anhydrase inhibitor, antihypertensive, anti-cancer, anti-depressant, calcium channel blocker, analgesic, opioid antagonist, antiplatel, anticoagulant, fibrinolytic, statin, adrenoceptor agonist, beta blocker, antihistamine, respiratory stimulant, micolytic, expertorant, benzodiazepine, barbiturate, anxiolytic, antipsychotic, tricyclic anti depressant, $5HT_1$ antagonist, opiate, 5HT, agonist, antiemetic, antiepileptic, dopaminergic, antibiotic, antifungal, anthelmintic, antiviral, antiprotozoal, antidiabetic, insulin, thyrotoxin, femal sex hormone, male sex hormone, antioestrogen, hypothalamic, pituitary hormone, posterior pituitary hormone antagonist, antidiuretic hormone antagonist, bisphosphonate, dopamine receptor stimulant, androgen, non-steroidal anti-inflammatory, immuno suppressant local anaesthetic, sedative, antipsioriatic, silver salt, topical antibacterial vaccine.

Embodiments of the present invention will now be described by way of examples below. The effects of type and ratios of PEG or PPG, PEG-PPG-PEG or PPG-PEG-PPG copolymer, diols and diisocyanates on the properties of polymers can be seen in the following Tables, Examples and Figures.

EXAMPLE 1

Polymer Manufacture

Various types of polyethylene glycols, polypropylene glycols, PEG-PPG-PEGs, PPG-PEG-PPGs, diols and diisocyanates, in a range of stoichiometric ratios were used to demonstrate their effect on the properties of the hydrophilic linear polyurethane elastomer polymers. PEG400, PEG900, PEG1000 and PEG2000 are polyethylene glycols having a molecular weight of 400, 900, 1000 and 2000 g/mol, respectively; PPG1000 and PPG2000 are polypropylene glycols having a molecular weight of 1000 and 2000 g/mol; PEG-PPG-PEG1100 and PEG-PPG-PEG4400 are block copolymers having a molecular weight of 1100 and 4400 g/mol; PPG-PEG-PEG2000 is a block copolymer having a molecular weight of 2000 g/mol; DD is 1,10-decanediol and DDD is 1,12-dodecanediol; DMDI is dicyclohexylmethane-4,4-diisocyanate and HMDI is 1,6-hexamethylene diisocyanate; $FeCl_3$ is Ferric chloride, DABCO is triethylene diamine and $SnOct_2$ is Stannous octoate.

Polymers were produced by applying the polymerisation method described in WO patent Publication WO2004029125. The PEG, PPG, PEG-PPG-PEG and/or PPG-PEG-PPG were melted and vacuum dried at 95° C. along with the diol and the catalyst (if used) in a rotary-evaporator for an hour at a pressure below 1 mbar. At this point the dried mixture was fed into a reactor prior to the diisocyanate addition. The manufactured polymers are shown in Table 1.

EXAMPLE 5

Solubility of Polymers in Different Solvents

A number of polymers from Table 1 were dissolved in different solvents in order to find suitable solvents. The solubility tests were carried out for 24 hours at room temperature (RT). The solubility results for the selected polymers are shown in Table 2.

TABLE 1

Manufactured hydrophilic thermoplastic polyurethane elastomers.

| | PEG | | PPG | | PEG-PPG-PEG | | PPG-PEG-PPG | | DD | | DDD | | DMDI | | HMDI | |
|---|---|---|---|---|---|---|---|---|---|---|---|---|---|---|---|---|
| Polymer Name | Mw | mol ratio | Mw | mol ratio | Mw | mol ratio | Mw | mol ratio | Mw | mol ratio | Mw | mol ratio | Mw | mol ratio | Mw | mol ratio |
| Polymer A | — | — | 1000 | 0.054 | 4400 | 0.046 | — | — | 174 | 1 | — | — | 262 | 1.1 | — | — |
| Polymer B | — | — | 1000 | 0.054 | — | — | 2000 | 0.046 | 174 | 1 | — | — | 262 | 1.1 | — | — |
| Polymer C | 400 | 0.216 | — | — | — | — | 2000 | 0.184 | 174 | 1 | — | — | 262 | 1.4 | — | — |
| Polymer D | 900 | 0.3 | 1000 | 0.3 | — | — | — | — | — | — | 202 | 0.3 | 262 | 0.9 | — | — |
| Polymer E | 2000 | 0.3 | 2000 | 0.3 | — | — | — | — | — | — | 202 | 0.3 | 262 | 0.9 | — | — |
| Polymer F | — | — | 1000 | 0.054 | 4400 | 0.046 | — | — | 174 | 1 | — | — | — | — | 168 | 1.1 |
| Polymer G | — | — | 1000 | 0.054 | — | — | 2000 | 0.046 | 174 | 1 | — | — | — | — | 168 | 1.1 |
| Polymer H*1 | — | — | 1000 | 0.054 | — | — | 2000 | 0.046 | 174 | 1 | — | — | — | — | 168 | 1.1 |
| Polymer I | — | — | 1000 | 0.054 | — | — | 2000 | 0.046 | — | — | 202 | 1 | — | — | 168 | 1.1 |
| Polymer J | 400 | 0.216 | — | — | 4400 | 0.184 | — | — | 174 | 1 | — | — | 262 | 1.4 | — | — |
| Polymer K | 400 | 0.216 | — | — | 4400 | 0.184 | — | — | — | — | 202 | 1 | — | — | 168 | 1.4 |
| Polymer L | 400 | 0.216 | — | — | 1100 | 0.184 | — | — | 174 | 1 | — | — | — | — | 168 | 1.4 |
| Polymer M*2 | 1000 | 0.2 | — | — | 1100 | 0.2 | — | — | 174 | 1 | — | — | — | — | 168 | 1.4 |
| Polymer N*3 | 1000 | 0.2 | — | — | 1100 | 0.2 | — | — | 174 | 1 | — | — | — | — | 168 | 1.4 |
| Polymer O | — | — | 2000 | 0.1 | — | — | 2000 | 0.1 | 174 | 1 | — | — | — | — | 168 | 1.2 |
| Polymer P | — | — | 2000 | 0.25 | — | — | 2000 | 0.25 | 174 | 1 | — | — | — | — | 168 | 1.5 |
| Polymer Q | — | — | 2000 | 1 | — | — | 2000 | 1 | 174 | 1 | — | — | — | — | 168 | 3 |
| Polymer R | 2000 | 0.25 | — | — | 2000 | 0.25 | — | — | 174 | 1 | — | — | — | — | 168 | 1.5 |

*1No catalyst
*2DABCO
*3DABCO + SnOct

EXAMPLE 2

Polymerisation Reaction as a Function of Time

The effect of polymerisation time on the polymer produced was investigated using triple detection Size Exclusion Chromatography (SEC). Molecular weight determination as a function of polymerisation time was carried out for Polymers B and C, see FIG. 1 below. The molecular weight of the polymer will determine the rheology, melt flow and mechanical properties of the polymer. Therefore the importance of determining molecular weight values is evident.

EXAMPLE 3

The Effect of the Catalyst on the Polymerisation Reactions

The polymerisations were performed as in Example 1 but the ferric chloride was replaced by DABCO and SnOct$_2$ for Polymer N (Table 1); while DABCO alone was used for Polymer M (Table 1). Polymer H (Table 1) was prepared in the absence of a catalyst.

EXAMPLE 4

The Use of Different Diisocyanates

The polymerisations were performed as in Example 1 but the DMDI was replaced by HMDI for polymers F, G, H, I, K, L, M, N, O, P, Q and R in Table 1.

TABLE 2

Polymer solubility in selected solvents.

| Polymer Name | DCM RT | THF 35° C. | DCM/TEA RT | THF/TEA 35° C. |
|---|---|---|---|---|
| Polymer A | — | YES | — | — |
| Polymer B | — | YES | — | — |
| Polymer C | — | YES | — | — |
| Polymer D | — | YES | — | — |
| Polymer P | YES | YES | YES | YES |

DCM dichloromethane
THF tetrahydrofuran
TEA triethyl amine

EXAMPLE 6

Swelling Capacity of Polymers in Different Solvents

The swelling determinations for a number of selected polymers were carried out in water, ethanol, isopropyl alcohol (IPA) and in a 50% mixture of IPA/water in order to measure the amount of solvent absorbed by the polymer. The results were calculated based on the average swelling of 10 specimens and are shown in Table 3. The formula used for the calculations is shown below:

$$\% \text{ Swelling} = \frac{\text{Swollen Weight} - \text{Dry Weight}}{\text{Dry Weight}} \times 100$$

TABLE 3

Percent swelling of the selected polymers in different swelling media (water, ethanol, IPA and 50% IPA/water).

| Polymer Name | % Swelling in Water | % Swelling in Ethanol | % Swelling in IPA | % Swelling in 50% IPA/water |
|---|---|---|---|---|
| Polymer A | 2.5 | 133 | 113 | 68 |
| Polymer B | 2.5 | 89 | 73 | 71 |
| Polymer C | 43 | N/A | 130 | 206 |

EXAMPLE 7

Shore Hardness Testing (Elasticity Measurement)

The manufactured polymers were tested for Shore hardness using durometers A and D. Durometers A and D are generally used to measure elasticity of soft and hard rubber, respectively. These measurements are well known to the skilled person in the field. The results are presented as the average of four measurements and are presented in Table 4.

TABLE 4

Shore hardness values determined for the manufactured polymers.

| | Durometer A | | Durometer D | |
|---|---|---|---|---|
| Polymer Name | Max Hardness | Creep (15 sec) | Max Hardness | Creep (15 sec) |
| Polymer A | 97.6 | 0.4 | 50.6 | 7.6 |
| Polymer B | 97.5 | 2.6 | 56.5 | 12.5 |
| Polymer C | 81.4 | 2.6 | 27.4 | 4.3 |
| Polymer D | N/A | N/A | N/A | N/A |
| Polymer E | N/A | N/A | N/A | N/A |
| Polymer F | 95.8 | 0.0 | 49.0 | 3.6 |
| Polymer G | 97.0 | 0.3 | 56.6 | 2.3 |
| Polymer H*1 | 97.0 | 0.0 | 60.5 | 4.0 |
| Polymer I | 97.0 | 2.5 | 53.8 | 4.8 |
| Polymer J | N/A | N/A | N/A | N/A |
| Polymer K | 88.3 | 20.0 | 22.8 | 10.0 |
| Polymer L | 85.3 | 0.9 | 39.3 | 1.5 |
| Polymer M*2 | 94.8 | 0.4 | 45.3 | 1.5 |
| Polymer N*3 | 95.4 | 3.8 | 40.3 | 6.3 |
| Polymer O | 89.8 | 1.8 | 39.8 | 4.1 |
| Polymer P | 88.0 | 3.8 | 28.1 | 1.6 |
| Polymer Q | 60.8 | 3.9 | N/A | N/A |
| Polymer R | 87.0 | 2.0 | 29.8 | 1.8 |

Experimental conditions:
Temperature 21° C.
Relative Humidity % RH 39

EXAMPLE 8

Polymer Films Manufactured by Compression Moulding

A number of selected polymers from Table 1 were dried over night under vacuum prior to the processing. The upper and lower plate temperatures of the compression moulding machine were set at the target processing temperature. Two Teflon sheets were placed between the mould and the hot plates. The melting time was 3-5 minutes followed by a 30-120 seconds holding under pressure (170-200 bars). A predetermined amount of polymer was used to fill the mould. After cooling to room temperature the samples (pessary devices with dimensions 30 mm×10 mm×1 mm) were mechanically punched out and kept in the freezer for further analysis. The film processing conditions are shown in Table 5.

TABLE 5

Thermal processing of the manufactured polymers using compression moulding.

| Polymer | Temperature (° C.) | Cylinder Pressure (Bar) | Melting Time (s) | Pressure Time (s) | Mould Thickness (mm) |
|---|---|---|---|---|---|
| Polymer A* | 160 | 200 | 240 | 120 | 1.0 |
| Polymer A* | 160 | 200 | 210 | 120 | 1.0 |
| Polymer A | 150 | 200 | 120 | 60 | 0.25 |
| Polymer C | 130 | 200 | 180 | 60 | 0.4 |

EXAMPLE 9

Drug Loading—Extrusion

Selected polymers were loaded with two different active compounds: fluconazole and oxybutynin. A 16 mm co-rotating twin-screw laboratory extruder was used for loading the polymers. Table 6 shows the drug loading conditions.

TABLE 6

Extrusion loading conditions used for the fluconazole loaded devices.

| Polymer Name | Drug | Drug (wt %) | Screw speed (rpm) | Temperature profile from feed to die (° C.) |
|---|---|---|---|---|
| Polymer A* | Fluconazole | 20 | 40 | 55-95-120-120-120 |
| Polymer A* | Fluconazole | 50 | 40 | 55-95-115-115-115 |
| Polymer A | Fluconazole | 20 | 60 | 80-110-110-110-110 |
| Polymer A | Fluconazole | 50 | 60 | 103-113-115-115-115 |
| Polymer A | Oxybutynin | 5 | 60 | 80-115-115-115-115 |
| Polymer A | Oxybutynin | 10 | 40 | 90-110-110-110-110 |
| Polymer A | Oxybutynin | 15 | 60 | 80-110-110-110-110 |
| Polymer B | Oxybutynin | 5 | 50 | 132-132-132-132-132 |
| Polymer B | Oxybutynin | 10 | 40 | 133-133-133-133-136 |
| Polymer C | Fluconazole | 20 | 60 | 95-115-115-115-115 |
| Polymer C | Oxybutynin | 5 | 60 | 85-100-105-105-105 |
| Polymer C | Oxybutynin | 10 | 50 | 80-100-105-105-105 |
| Polymer C | Oxybutynin | 15 | 40 | 80-100-110-110-110 |

Two different batches of the same polymer composition (Polymer A and A*) were loaded with fluconazole in two different drug amounts in order to prove the reproducibility of the polymerisation process. Release results were found to be reproducible.
The quantity of the active compound loaded into the polymers was based on the required therapeutic dosage.

EXAMPLE 10

Drug Release Studies—Effect of Polymer

In vitro drug release properties of the extrusion loaded polymers were determined by dissolution studies. The amount of fluconazole and oxybutynin released from the extrusion loaded polymers was investigated by using dissolution method based on the USP paddle method for short term release and incubator shaker method with Erlenmeyer bottles for long term release. USP paddle technique is comprised of an automated UV dissolution system where a Distek (2100C model) dissolution paddle (speed 50 rpm) is connected to a Unicam UV 500 spectrophotometer via an Icalis peristaltic pump. The system is operated using Dsolve software. In the incubator shaker method the samples were taken manually and the Unicam UV 500 spectrophotometer was used to analyse the samples.

Experimental conditions:
Temperature 37° C.
Dissolution media 500 ml of deionised degassed water In this example the effect of the polymer structure on the release of fluconazole was investigated. Polymer A and C were loaded with 20 wt % fluconazole and Polymer A, B and C were loaded with 5% of oxybutynin using extrusion techniques. The release of fluconazole and oxybutynin varied depending on the polymer matrix, see FIGS. 2a and 2b.

EXAMPLE 11

Drug Release Studies—Effect of Drug

When the drug type was changed different release profiles were obtained. Fluconazole and oxybutynin were loaded into Polymer A. Normalised dissolution profiles are shown in FIG. 3. The same dissolution method as in Example 10 was used to determine the release curves.

EXAMPLE 12

Drug Release Studies—Effect of Drug Amount

The effect of increasing loading content was investigated by dissolution studies. The effect of different drug contents on the release properties of Polymer A was investigated and is shown in FIG. 4. The fluconazole loading was increased from 20 wt % to 50 wt %. The same dissolution method as in Example 10 was used to determine the release curves.

EXAMPLE 13

Drug Release Studies—Comparison with High-Swelling Polymers

The fluconazole release profile obtained for Polymer A and Polymer C were compared with the release profiles obtained for a crosslinked and a linear high-swelling polyurethane polymer, see FIG. 5. The diffusion loaded crosslinked polymer (crosslinked 17 wt % fluconazole) was from patent EP0016652/EP0016654. While the linear high swelling polymer was from patent WO2004029125 and was loaded using diffusion (high % SW 17 wt % fluconazole) as well as extrusion techniques (high % SW 20 wt % fluconazole). The same dissolution method as in Example 10 was used to determine the release curves. These new polymers can provide an excellent control over drug release, see FIG. 5.

What is claimed is:

1. A controlled release composition, comprising: (I) a water-swellable linear polymer obtained by reacting: (i) a polyethylene glycol; (ii) a polypropylene glycol; (iii) a diol; and (iv) a diisocyanate; and (II) a pharmaceutically active agent; wherein the molar ratio of the components (i), (ii), (iii) and (iv) is in the range 0.01-1 to 0.01-1 to 1 to 1.02-3, respectively.

2. The composition of claim 1, wherein the polyethylene glycol is a linear polyethylene glycol having a molecular weight of 400 g/mol to 2000 g/mol.

3. The composition of claim 1, wherein the polypropylene glycol is a linear polypropylene glycol having a molecular weight of 400 g/mol to 2000 g/mol.

4. The composition of claim 1, wherein the diol is a $C_5$ to $C_{20}$ diol.

5. The composition of claim 1, wherein the diol is a $C_8$ to $C_{15}$ diol.

6. The composition of claim 1, wherein the diol is 1,6-hexanediol, 1,10-decanediol, 1,12-dodecanediol or 1,16-hexadecanediol.

7. The composition of claim 1, wherein the diisocyanate is dicyclohexylmethane-4,4-diisocyanate, diphenylmethane-4,4-diisocyanate, or 1,6-hexamethylene diisocyanate.

8. The composition of claim 1, wherein the molar amount of component (iv) is equal to the combined molar amounts of components (i), (ii), and (iii).

9. The composition of claim 1, wherein the composition is in a solid dosage form.

10. The composition of claim 9, wherein the solid dosage form is a suppository, a ring or pessary for vaginal use, a buccal insert, or a transdermal patch.

11. The composition of claim 9, wherein the composition is an implant.

12. A controlled release composition, comprising (I) a water-swellable linear polymer obtained by reacting: (i) a polyethylene glycol; (ii) a polypropylene glycol; (iii) a diol; and (iv) dicyclohexylmethane-4,4-diisocyanate; and (II) a pharmaceutically active agent; wherein the molar ratio of components (i), (ii), (iii) and (iv) is 1:1:1:3.

13. The composition of claim 12, wherein the polyethylene glycol has a molecular weight of 900 g/mol.

14. The composition of claim 12, wherein the polyethylene glycol has a molecular weight of 2000 g/mol.

15. The composition of claim 12, wherein the polypropylene glycol has a molecular weight of 1000 g/mol.

16. The composition of claim 12, wherein the polypropylene glycol has a molecular weight of 2000 g/mol.

17. The composition of claim 12, wherein the diol is 1,12-dodecanediol.

* * * * *